United States Patent
Lindberg et al.

(10) Patent No.: US 7,735,488 B2
(45) Date of Patent: Jun. 15, 2010

(54) TRACHEAL INSERT ALLOWING PASSAGE OF A SELECTED SUBSTANCE

(75) Inventors: Lars Lindberg, Lund (SE); Georgios Psaros, Tullinge (SE); Göran Rydgren, Bunkeflostrand (SE)

(73) Assignee: Maquet Critical Care AB, Solna (SE)

( * ) Notice: Subject to any disclaimer, the term of this patent is extended or adjusted under 35 U.S.C. 154(b) by 1117 days.

(21) Appl. No.: 10/725,304

(22) Filed: Dec. 1, 2003

(65) Prior Publication Data

US 2004/0199108 A1 Oct. 7, 2004

(30) Foreign Application Priority Data

Dec. 4, 2002 (SE) .................................. 0203590

(51) Int. Cl.
*A61M 16/00* (2006.01)
*A61M 31/00* (2006.01)
*A61M 29/00* (2006.01)
*A61B 5/00* (2006.01)

(52) U.S. Cl. ............................ 128/207.14; 128/207.15; 600/309; 604/96.01; 604/97.01; 604/103.01

(58) Field of Classification Search ................................
128/207.14–207.18, 200.24, 200.26, 204.24;
600/529–533, 537, 538, 345–350, 309; 424/423;
604/96, 101, 264, 280, 281, 103.01, 103.02
See application file for complete search history.

(56) References Cited

U.S. PATENT DOCUMENTS

| | | | |
|---|---|---|---|
| 4,141,364 A * | 2/1979 | Schultze ................ 128/207.15 |
| 4,417,576 A | 11/1983 | Baran | |
| 4,624,261 A | 11/1986 | Hölscher | |
| 5,487,383 A | 1/1996 | Lavinson | |
| 5,533,516 A * | 7/1996 | Sahatjian .................... 600/562 |
| 5,536,241 A * | 7/1996 | Zapol ......................... 604/23 |
| 5,800,392 A | 9/1998 | Racchini | |
| 5,957,839 A * | 9/1999 | Kruse et al. ................. 600/309 |
| 5,985,307 A | 11/1999 | Hanson et al. | |
| 6,020,307 A | 2/2000 | Egan et al. | |
| 6,095,966 A | 8/2000 | Chornenky et al. | |
| 6,183,418 B1 | 2/2001 | Kuennecke | |
| 6,242,472 B1 | 6/2001 | Sekins et al. | |
| 6,328,711 B1 | 12/2001 | Guibert et al. | |
| 6,660,833 B1 * | 12/2003 | Walther et al. ............. 530/324 |
| 6,737,243 B1 * | 5/2004 | Ise et al. .................... 435/7.92 |
| 6,761,172 B2 * | 7/2004 | Boussignac et al. .... 128/207.14 |
| 6,802,317 B2 * | 10/2004 | Gobel ................... 128/207.14 |
| 6,923,176 B2 * | 8/2005 | Ranzinger ............. 128/200.26 |
| 2007/0137621 A1 * | 6/2007 | Kimura et al. .............. 123/490 |

* cited by examiner

*Primary Examiner*—Danton DeMille
(74) *Attorney, Agent, or Firm*—Schiff Hardin LLP

(57) ABSTRACT

A medical device has a cuff adapted to be positioned in the trachea of a subject with a patient tube, and a first tube having a distal end coupled to the cuff and a proximal end communicable with the surroundings. More effective and simpler sample taking and/or dosing of medicament is achieved by a second tube that is coupled with a distal end to the cuff and communicable with the surroundings via a proximal end, together with a pumping device that is connected to the proximal end of the first tube and to the proximal end of the second tube in order to circulate a fluid through the cuff. The cuff has a membrane that is permeable to a specific substance, the membrane being disposed to allow transfer of the specific substance between the interior and the exterior of the cuff.

5 Claims, 2 Drawing Sheets

TRACHEAL INSERT ALLOWING PASSAGE OF A SELECTED SUBSTANCE

BACKGROUND OF THE INVENTION

1. Field of the Invention

The present invention relates to a medical device according to the preamble of claim 1.

2. Description of the Prior Art

A substance known as surfactant is found in healthy lungs. An essential function performed by surfactant is the reduction of surface tension so that all of the alveoli can be kept open. Surfactant contains a number of proteins, the individual functions of which are not entirely understood. The main constituents, however, are known and include four different proteins. These proteins are usually named SP-A, SP-B, SP-C, and SP-D.

Different types of lung trauma influence the occurrence of surfactant, such as by a reduction in the total amount of surfactant (the creation of surfactant in the lungs is influenced) and in part by a change in the occurrence of one or more of the main proteins SP-A, SP B, SP-C, and SP-D. The consequence of the change in the occurrence of surfactant is in most cases a stiffer (less pliant) lung, often with an unknown number of alveoli that have collapsed. Gas exchange is quickly worsened as a result and the patient risks becoming dependent on mechanical ventilation in order to survive.

A more complete background description of the role played by surfactant and the physiological interplay is provided in U.S. Pat. No. 6,020,307.

An obvious treatment of surfactant deficiency is to supply exogenous surfactant, however this is not entirely without consequence. A completely synthetic surfactant is presently unavailable. Natural surfactant is manufactured from animal lungs but is expensive. The price of natural surfactant is in the region of £200 per milliliter (ml). The recommended dosage is 1.25 ml per kilogram bodyweight. For a child weighing 2 kg the cost of one dose is circa £500 but for an adult of 60 kg the cost of a dose is closer to £15,000. Dosing normally needs repeating several times during a treatment. Natural surfactant therefore cannot be used as a general treatment method, at least not for adult patients. At the same time it is true that a portion of the exogenous surfactant is forced from the lungs during expiration. This is at least in part due to the change in alveolar volume during expiration. It can also be assumed that a part of the added surfactant never reaches the alveoli and do not provide any therapeutic effect.

Although analysis methods are known to distinguish between the different proteins it is not possible to undertake continual or frequent analysis of the condition for every single patient. This is primarily because samples of surfactant are extracted from the lungs using bronchial washes or mucous suction. Both of these methods normally involve the discontinuation of the mechanical ventilation of the patient and in the worst case the patient must be disconnected from the ventilator.

There therefore exists a desire to improve the management of surfactant deficiency. A first goal is to provide more effective procedures that make possible less expensive and more effective treatment. A second goal is better and more effective sample taking that can be carried out relatively continuously. A third goal is a better and more effective means for the dosing of surfactant.

Additionally, sampling of substances related to the function and/or condition of the lungs may relate to substances other than the surfactant components mentioned above.

SUMMARY OF THE INVENTION

It is and object of the present invention to provide a medical device adapted for insertion in the trachea of a subject wherein the above-discussed problems associated with conventional devices of this type are alleviated or avoided.

This object is achieved in accordance with the present invention in a medical device having a cuff adapted for positioning in the trachea of a subject with a patient tube, and having a first tube with a first end coupled to the cuff and a second end, and a second tube having a first end coupled to the cuff and a second end, and a pumping device connected between the respective second ends of the first and second tubes to circulate a fluid through the cuff, and wherein the cuff has a membrane that is permeable to a specific substance, the membrane being disposed to allow transfer of the specific substance between an interior of the cuff and an exterior of the cuff.

Cuffs usually are used to fix a tracheal tube in the trachea and to seal the gap between the tube and the trachea. Such a cuff usually is inflated by air supplied through a tube.

In accordance with the invention a second tube is instead connected to the cuff to allow a fluid to be circulated through the cuff. A permeable membrane is also arranged in the cuff so that specific substances that are to be analyzed (or dosed) can pass through the membrane, while the fluid does not.

By circulating a sufficiently large volume of fluid the cuff can still be fixed and sealed against the trachea but it is clear that the cuff according to the invention may even be formed as a separate cuff (arranged below the usual cuff) that entirely or partly consists of the membrane. Such a separate cuff has no sealing function, rather it can be configured to be surrounded by mucous and secretions to as high a degree as is possible.

By forcing the specific substances, for example proteins, through the membrane and into the fluid, an analysis unit that quantitatively and qualitatively identifies one or more of the proteins SP-A, SP-B, SP-C, and SP-D can be connected. It is immaterial which known analysis method is employed. It is for example known to use monoclonal antibodies in different ways.

From the analysis a calculation unit can determine if a protein insufficiency exists and how large the dose of the protein should be to counter the insufficiency. It is an advantage for this purpose if the body mass of the patient is known.

Conversely, proteins may be dosed through the membrane to the patient. A suitable dose of a protein may be administered by a dosing unit. The dosing unit can, for this purpose, have reservoirs for the proteins that should be available for supply and, dependent on the analysis of the protein insufficiency, it supplies a therapeutically effective dose of one or more of the proteins into the fluid.

It should be noted that since the passage of protein through the membrane is in principle regulated by the difference in partial pressures on either side, the protein composition in the patient can be automatically regulated/compensated by allowing a relatively low flow of a fluid having the "correct" composition of proteins. If an insufficiency exists in the patient then this protein will pass through the membrane. The greater the insufficiency then the greater the diffusion rate. The returned fluid can, if desired, be analyzed in order to quantitatively and qualitatively establish which of the proteins has been transferred to the patient. The returned fluid can be filtered and by the addition of proteins restored to the "correct" composition.

The cuff may be divided into two or more chambers, each one having a fluid flowpath therethrough and each having a permeable membrane.

Analysis and dosing may be done using separate chambers, which may be an advantage if it is desired to use different fluids (or to simultaneously dose other medicaments).

Alternatively, each chamber in the cuff may be adapted for a specific protein, or a specific type of protein. For example SP-B and SP-C are fat-soluble while SP-A and SP-D are water-soluble. Different fluids can increase the effectiveness of the analysis/dosing.

It is also known that an alignment effect on the proteins that normally pass through the membrane can be achieved using well-defined nano-tubes across which a suitable voltage is established. One can thereby select the direction of protein transport or alternatively can select which protein shall be permitted into a specific chamber. It also is possible to prepare a tracheal tube with a cuff with different proteins in high concentrations that are relapsed into the trachea by means of a voltage applied across the membrane.

DESCRIPTION OF THE PREFERRED EMBODIMENTS

Figure 1:
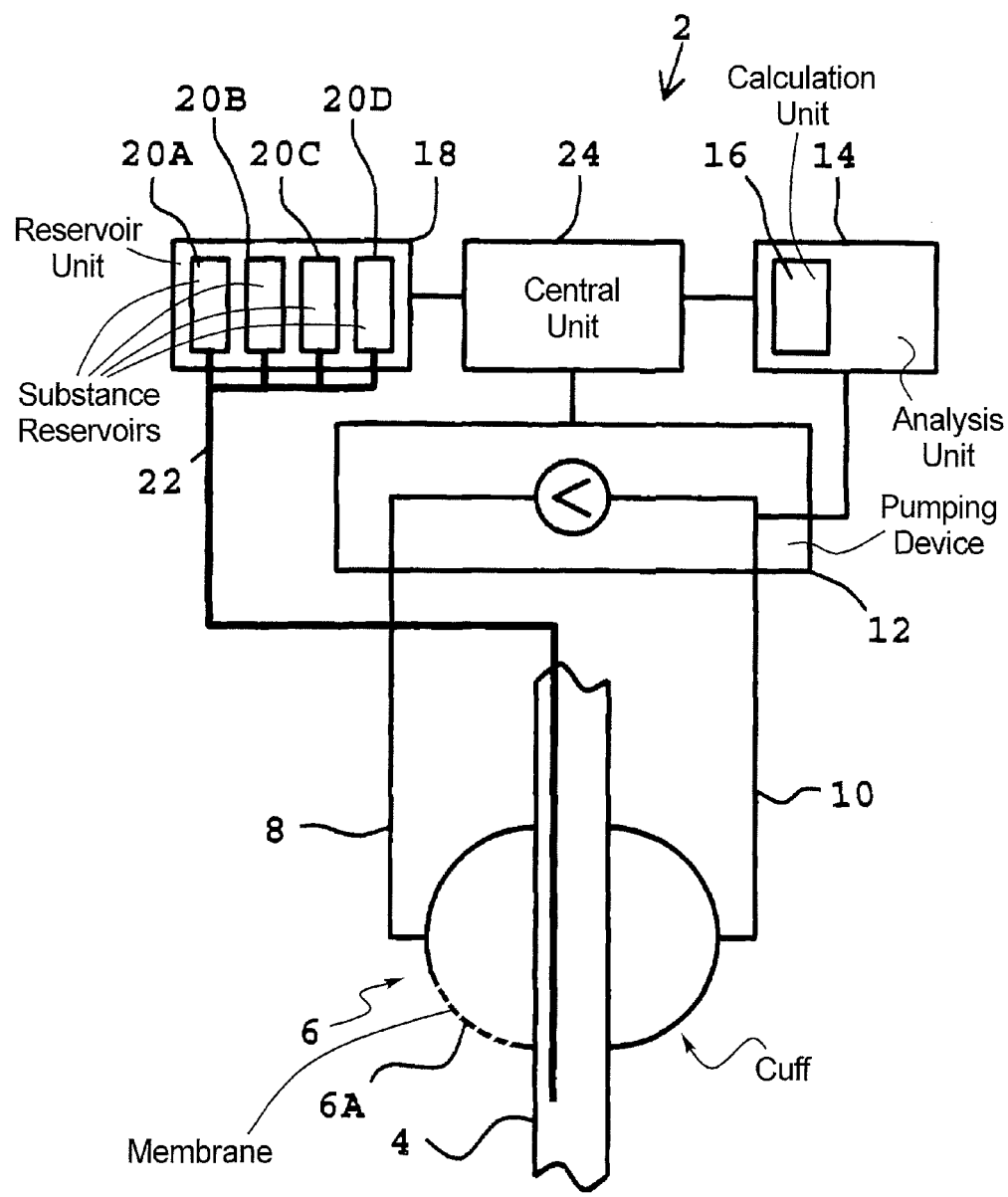
FIG. 1 shows an embodiment of a medical device according to the invention.

An embodiment of a medical device 2 according to the invention is shown in FIG. 1. The medical device 2 may include or be connected to a tube 4, preferably a tracheal tube. The tube 4 is to be dimensioned for location in the trachea of a patient (not shown). "Patient" means both animals and humans.

A cuff 6 is located on the tube 4. The cuff 6, in the present embodiment, is designed to be located below a conventional cuff. Alternatively, the cuff 6 may be formed to locate the tube 4 in the trachea and to seal the gap between the tube 4 and the trachea.

A first tube 8 conducts fluid down to the cuff 6 and a second tube 10 conducts fluid from the cuff 6. The fluid may be circulated at a known rate by a pumping device 12. The pumping device 12 may include a reservoir (not shown) for the fluid.

It is obviously not essential that the fluid be re-circulated to the cuff 6. New fluid may be supplied the whole time. This, however, results in a larger fluid usage.

In the present embodiment a portion of outward facing surface of the cuff 6 is formed of a permeable membrane 6A. This is sufficient to achieve the intended effect but it is possible for the entire outward facing surface to be formed of a permeable membrane. The membrane 6A is selectively permeable to one or more of the main proteins in the surfactant, designated as SP-A, SP-B, SP-C and SP-D.

Mucous and fluids will collect around the cuff 6 and if any of the proteins SP-A, SP-B, SP-C and SP-D are present externally of the cuff 6, the partial pressures will cause the proteins to pass through the membrane 6A into the fluid in the cuff 6. Protein-containing fluid then flows through the second tube 10.

The fluid is analyzed in an analysis unit 14, connected to the pumping device 12, in order to qualitatively and quantitatively determine the level of the respective protein.

There exist many known measurement techniques for the determination of the presence of the different proteins. Antibodies, selectively chosen for a particular protein, are common and may be used on nano-spheres that flow with the fluid. The presence of the proteins may then be determined by fluorescence means of an appropriate light source within the analysis unit 14.

If desired, the nano-spheres can be marked with different color substances dependent on the selected antibody and thereby permit a simultaneous measurement and analysis of all the desired proteins.

The determination of whether there is a deficiency of protein (and in that case the extent of the deficiency) is carried out in a calculation unit 16 in the analysis unit 14.

When it has been established that one or more of the proteins SP-A, SP-B, SP-C and SP-D is/are not present in a sufficient amount a therapeutically effective dose of this/these protein(s) can be determined and dosed to the patient from a dosing unit 18. In the present example this is achieved via a dosing tube 22 to the patient's trachea and further down to the lungs.

The dosing unit 18 has a first reservoir 20A for SP-A, a second reservoir 20B for SP-B a third reservoir 20C for SP-C and a fourth reservoir 20D for SP-D. The determined doses of the proteins SP-A, SP-B, SP-C and SP-D can be dosed from respective reservoirs 20A-D via the dosing tube 22 to the patient.

A user interface, internal communications within the device, regulation and monitoring and other functions that can be provided, included in a central unit 24.

The medical device 2 may even be simplified if the intention is to only maintain a balance in the protein occurrence. The dosing unit 18 then can deliver doses of the respective protein that corresponds to the normal occurrence in the lung. The membrane 6A in the cuff 6 will automatically help to attain an equalization. Protein that is missing or that exists at much lower levels than normal will produce a large partial pressure difference and will quickly migrate through the membrane 6A. Protein that is already found in normal amounts in the lungs is in equilibrium with the dosed amount and no exchange will occur through the membrane 6A.

If the re-use of the fluid or the proteins that have not diffused into the body is desired then the liquid that has been taken from the cuff 6 can be analyzed to determine its composition. Those proteins that have diffused can be replaced (via the dosing unit 18) and the fluid returned to the cuff 6. At the same time the analysis gives a measure of which proteins are missing and to what extent (quantity) they are missing.

Figure 2:
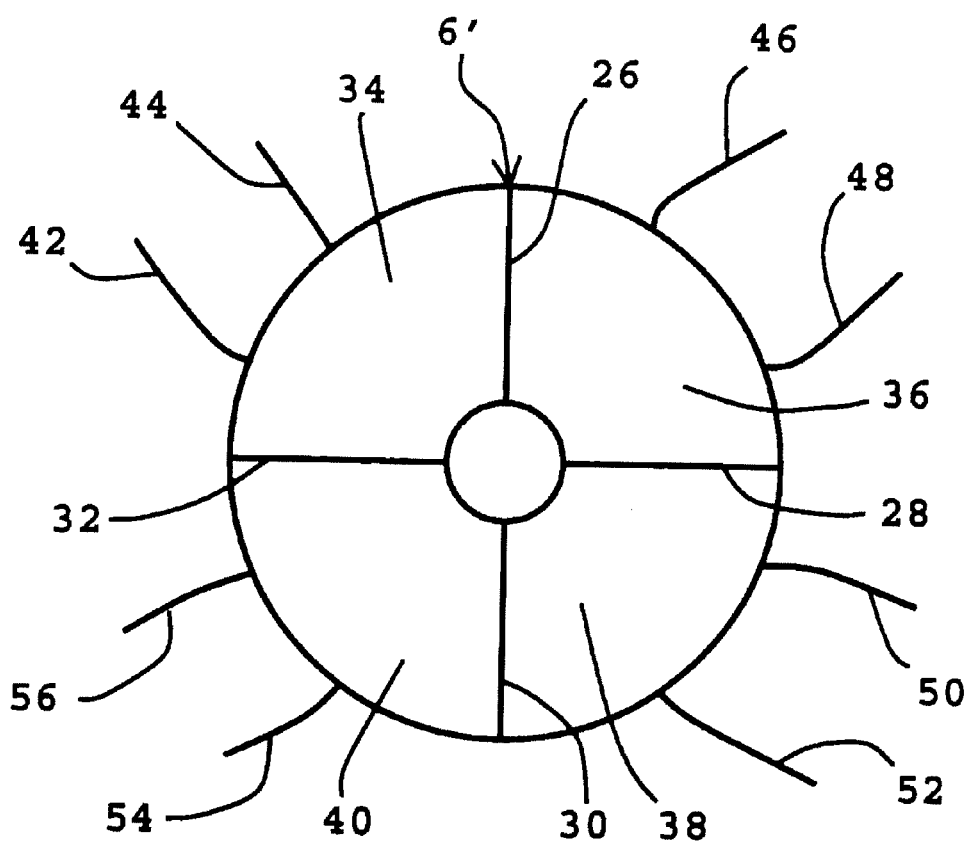
FIG. 2 shows an alternative arrangement of a cuff.

An alternative design of a cuff 6' is illustrated in FIG. 2. The cuff 6' has a first partition wall 26, a second partition wall 28, a third partition wall 30, and a fourth partition wall 32. These partition walls partition the cuff 6' into a first chamber 34, a second chamber 36, a third chamber 38 and a fourth chamber 40.

The first chamber 34 is connected to a first tube 42 and a second tube 44 for the circulation of fluid through the first chamber 34. The second chamber 36 is connected to a third tube 46 and a fourth tube 48 for the circulation of fluid through the second chamber 36. The third chamber 38 is connected to a fifth tube 50 and to a sixth tube 52 for the circulation of fluid through the third chamber 38. The fourth chamber 40 is connected to a seventh tube 54 and to an eighth tube 56 for the circulation of fluid through the fourth chamber 40.

The partitioning of the cuff 6' into multiple chambers 34, 36, 38, 40 provides in many possibilities for use.

One use is that every chamber 34, 36, 38, 40 can be specifically designed for one protein. The membrane, fluid, analysis method and dosing can all be individually adapted for one protein at the same time as all the proteins are handled.

Alternatively, the analysis and the dosing may be performed in different chambers. For example, the proteins SP-A and SP-D, which are water-soluble, can be analyzed using the first chamber 34 and dosed using the third chamber 38 while the proteins SP-B and SP-C, which are fat soluble, can be analyzed using the second chamber 36 and dosed via the fourth chamber 40.

It is clear that a different number of chambers may be employed. It is also clear that the medical device may be used for one or more proteins. Likewise components of the surfactant other than the aforementioned proteins may be handled. Other substances (beyond those that are found in surfactant) can be diffused through for analysis and dosing.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical device comprising:
   a tracheal tube and a cuff surrounding an exterior of said tracheal tube and configured to be positioned in the trachea of a subject with the tracheal tube allowing the subject to respirate through the tracheal tube;
   a first tube having a first end in fluid communication with an interior of the cuff and having an opposite, second end;
   a second tube having a first end in fluid communication with the interior of the cuff and having an opposite, second end;
   a pumping device connected to the respective second ends of the first and second tubes that circulates a fluid through the interior of the cuff, said pump, said first and second tubes, and said cuff forming a flow path for said fluid;
   said cuff comprising a membrane that is selectively permeable to a substance relative to said fluid, said membrane being disposed to allow transfer through said membrane of said substance from an exterior of the cuff to the interior of the cuff so as to mix with the fluid in the interior of the cuff;
   an analysis unit in fluid communication with said flow path that analyzes said fluid with regard to content in said fluid of said substance from the exterior of the cuff that has mixed with said fluid the interior of the cuff;
   a dosing unit in fluid communication with said flow path that administers a dose of a medicament into said fluid; and
   said analysis unit comprising a calculation unit that quantitatively determines an amount of said substance in said fluid relative to a predetermined normal amount, and said dosing unit comprising at least one reservoir containing at least one additive corresponding to said substance, said dosing unit causing said additive from said reservoir to be added into said medicament if said analysis unit determines that said amount of said substance in said fluid is below said predetermined normal amount.

2. A medical device as claimed in claim 1 wherein said analysis unit includes a calculation unit that quantitatively determines an amount of said substance in said fluid relative to a predetermined normal amount.

3. A medical device as claimed in claim 1 wherein said cuff comprises at least one partition wall that partitions the interior of said cuff into multiple chambers, each chamber having a first chamber tube with a first chamber tube end in fluid communication therewith and a second chamber tube with a first chamber tube end in fluid communication therewith, and wherein said first chamber tube has a second chamber tube end and said second chamber tube has a second chamber tube end in fluid communication with said pumping device for circulation of respectively separate fluids through the multiple chambers.

4. A medical device as claimed in claim 1 wherein said membrane is permeable to at least one protein, as said substance, selected from the group of proteins consisting of SP-A, SP-B, SP-C and SP-D that are present in surfactant.

5. A medical device as claimed in claim 1 wherein said membrane also allows transfer through said membrane of said substance from the interior of the cuff to the exterior of the cuff and wherein said analysis unit, after said dosing unit includes said additive in said medicament, analyzes said fluid with regard to content in said fluid of said substance that has mixed with said fluid from said exterior of the cuff and from said medicament.

* * * * *